United States Patent
Kelman et al.

(10) Patent No.: US 9,308,300 B2
(45) Date of Patent: Apr. 12, 2016

(54) PROSTHETIC IMPLANTS

(75) Inventors: David C. Kelman, Collierville, TN (US); Hamish Forster, Memphis, TN (US); Malcolm Brown, Otley (GB); Horacio Montes De Oca Balderas, York (GB); Mason James Bettenga, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1073 days.

(21) Appl. No.: 12/596,659

(22) PCT Filed: Apr. 16, 2008

(86) PCT No.: PCT/US2008/060458
§ 371 (c)(1),
(2), (4) Date: Jun. 22, 2010

(87) PCT Pub. No.: WO2008/130989
PCT Pub. Date: Oct. 30, 2008

(65) Prior Publication Data
US 2010/0262144 A1   Oct. 14, 2010

Related U.S. Application Data

(60) Provisional application No. 60/912,694, filed on Apr. 19, 2007.

(51) Int. Cl.
*A61F 2/34* (2006.01)
*A61L 31/10* (2006.01)
(Continued)

(52) U.S. Cl.
CPC . *A61L 31/10* (2013.01); *A61F 2/34* (2013.01); *A61F 2/3603* (2013.01); *A61F 2/3609* (2013.01); *A61F 2/3662* (2013.01); *A61F 2/38* (2013.01); *A61F 2/4081* (2013.01);
(Continued)

(58) Field of Classification Search
CPC ........... A61B 17/0401; A61B 17/0642; A61B 2017/00867; A61B 2017/00871; A61F 2002/30062; A61F 2210/0014
USPC ........................................................ 623/23.58
See application file for complete search history.

(56) References Cited

U.S. PATENT DOCUMENTS 3,856,905 A   12/1974  Dawson
3,926,459 A   12/1975  Pontigny
(Continued)

FOREIGN PATENT DOCUMENTS

DE   1604403 B1   11/1970
DE   3036611 A1   6/1982
(Continued)

OTHER PUBLICATIONS

International Search Report mailed Aug. 7, 2009, which was received in parent application No. PCT/US2008/060821, 11 pages.
(Continued)

*Primary Examiner* — Bruce E Snow
*Assistant Examiner* — Melissa Hoban
(74) *Attorney, Agent, or Firm* — Taft Stettinius & Hollister LLP

(57) ABSTRACT

The present disclosure relates to prosthetic implants, components of prosthetic implants, and methods of fixating the components to one another and, especially fixation of the implants to bone.

23 Claims, 10 Drawing Sheets

(51) Int. Cl.

| | |
|---|---|
| *A61F 2/36* | (2006.01) |
| *A61F 2/38* | (2006.01) |
| *A61F 2/40* | (2006.01) |
| *A61L 27/34* | (2006.01) |
| *A61L 27/56* | (2006.01) |
| *A61L 27/58* | (2006.01) |
| *A61L 31/14* | (2006.01) |
| *A61F 2/30* | (2006.01) |
| *A61F 2/48* | (2006.01) |
| *A61B 17/00* | (2006.01) |

(52) U.S. Cl.
CPC ............... *A61L 27/34* (2013.01); *A61L 27/56* (2013.01); *A61L 27/58* (2013.01); *A61L 31/146* (2013.01); *A61L 31/148* (2013.01); *A61B 2017/00287* (2013.01); *A61B 2017/00871* (2013.01); *A61F 2002/30034* (2013.01); *A61F 2002/30064* (2013.01); *A61F 2002/30067* (2013.01); *A61F 2002/30072* (2013.01); *A61F 2002/3082* (2013.01); *A61F 2002/30092* (2013.01); *A61F 2002/30095* (2013.01); *A61F 2002/30347* (2013.01); *A61F 2002/30457* (2013.01); *A61F 2002/30474* (2013.01); *A61F 2002/30484* (2013.01); *A61F 2002/30485* (2013.01); *A61F 2002/30579* (2013.01); *A61F 2002/30677* (2013.01); *A61F 2002/30738* (2013.01); *A61F 2002/30878* (2013.01); *A61F 2002/3412* (2013.01); *A61F 2002/3451* (2013.01); *A61F 2002/365* (2013.01); *A61F 2002/482* (2013.01); *A61F 2210/0014* (2013.01); *A61F 2210/0023* (2013.01); *A61F 2220/0025* (2013.01); *A61F 2220/0033* (2013.01); *A61F 2220/0058* (2013.01); *A61F 2250/0031* (2013.01); *A61F 2310/00011* (2013.01)

(56) References Cited

U.S. PATENT DOCUMENTS

| | | | |
|---|---|---|---|
| 4,950,258 A | | 8/1990 | Kawai et al. |
| 5,108,289 A | | 4/1992 | Fukuyo |
| 5,578,034 A | * | 11/1996 | Estes .............................. 606/281 |
| 5,951,288 A | | 9/1999 | Sawa |
| 6,080,161 A | * | 6/2000 | Eaves et al. ...................... 606/76 |
| 6,160,084 A | | 12/2000 | Langer et al. |
| 6,162,257 A | * | 12/2000 | Gustilo et al. ............. 623/22.32 |
| 6,277,390 B1 | | 8/2001 | Schaffner |
| 6,281,262 B1 | | 8/2001 | Shikinami |
| 6,299,448 B1 | | 10/2001 | Zdrahala et al. |
| 8,062,294 B2 * | | 11/2011 | Reynolds ......................... 606/60 |
| 8,585,770 B2 * | | 11/2013 | Meridew et al. ............ 623/23.46 |

| | | | |
|---|---|---|---|
| 2003/0130742 A1 * | 7/2003 | Connelly et al. ............ 623/23.35 |
| 2004/0030341 A1 | 2/2004 | Aeschlimann et al. |
| 2004/0220672 A1 * | 11/2004 | Shadduck .................. 623/17.16 |
| 2005/0234540 A1 * | 10/2005 | Peavey et al. ................ 623/1.18 |
| 2006/0201519 A1 * | 9/2006 | Frazier et al. .................. 128/848 |
| 2007/0083205 A1 | 4/2007 | Attawia et al. |
| 2007/0213828 A1 * | 9/2007 | Trieu et al. .................. 623/17.11 |
| 2007/0260249 A1 * | 11/2007 | Boyajian et al. ................ 606/72 |
| 2008/0208265 A1 * | 8/2008 | Frazier et al. .................. 606/326 |
| 2009/0149856 A1 | 6/2009 | Paakinaho et al. |
| 2012/0083895 A1 * | 4/2012 | Conway et al. ............ 623/22.35 |

FOREIGN PATENT DOCUMENTS

| | | |
|---|---|---|
| DE | 102005032005 A1 | 1/2007 |
| EP | 1000958 A1 | 5/2000 |
| FR | 2863478 A1 | 6/2005 |
| GB | 1416575 A | 12/1975 |
| JP | 09234241 A | 9/1997 |
| WO | 9622061 A1 | 7/1996 |
| WO | 2008131197 A1 | 10/2008 |

OTHER PUBLICATIONS

Nulend, et al., "Increased Calcification of Growth Plate Cartlidge as a Result of Compressice Force in Vitro," Arthritis & Rheumatism, 29(8):1002-1009(1986), 13 pages.

Nulend, et al., "Inhibition of Osteoclastic Bone Resorption by Mechanical Stimulation in Vitro," Arthritis & Rheumatism, 33(1):66-72 (1999), 11 pages.

International Preliminary Report on Patentability mailed Oct. 20, 2009, which was received in corresponding application No. PCT/US2008/060821, 9 pages.

English Patent Abstract of DE 102005032005 from esp@cenet, Publication Date Jan. 11, 2007.

Shen, et al., "Irradiation of Chemically Crosslinked Ultrahigh Molecular Weight Polyethylene," Journal of Polymer Science: Part B: Polymer Physics, vol. 34, 1063-1077 (1996), 15 pages.

Narkis, et al., "Some Properties of Silane-Grafted Moisture-Crosslinked Polyethylene," Polymer Engineering and Science, Sep. 1985, vol. 25, No. 13, 6 pages.

Gugumus, "Possibilities and limits of synergism with light stabilizers in polyolefins 2. UV absorbers in polyolefins," Polymer Degradation and Stability 75 (2002) 309-320, 12 pages.

Costa, et al., "Mechanisms of Crosslinking, Oxidative Degradation and Stabilization of UHMWPE," UHMWPE Biomaterials Handbook, Chapter 21, Copyright 2009, 15 pages.

Al-Malaika, et al., "Processing Effects on Antioxidant Transformation and Solutions to the Problem of Antioxidant Migration," Advances in Chemistry, American Chemical Society: Washington, DC, May 5, 1996, 15 pages.

English Patent Abstract of FR 2863478 from esp@cenet, published Jun. 17, 2005, 1 page.

Australian Examination Report No. 1; Australian Patent Office; Australian Patent Application No. 2014213578; Dec. 11, 2014; 3 pages.

\* cited by examiner

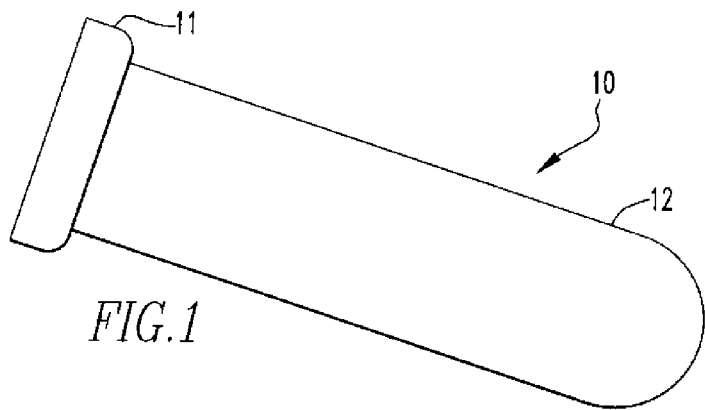
FIG.1
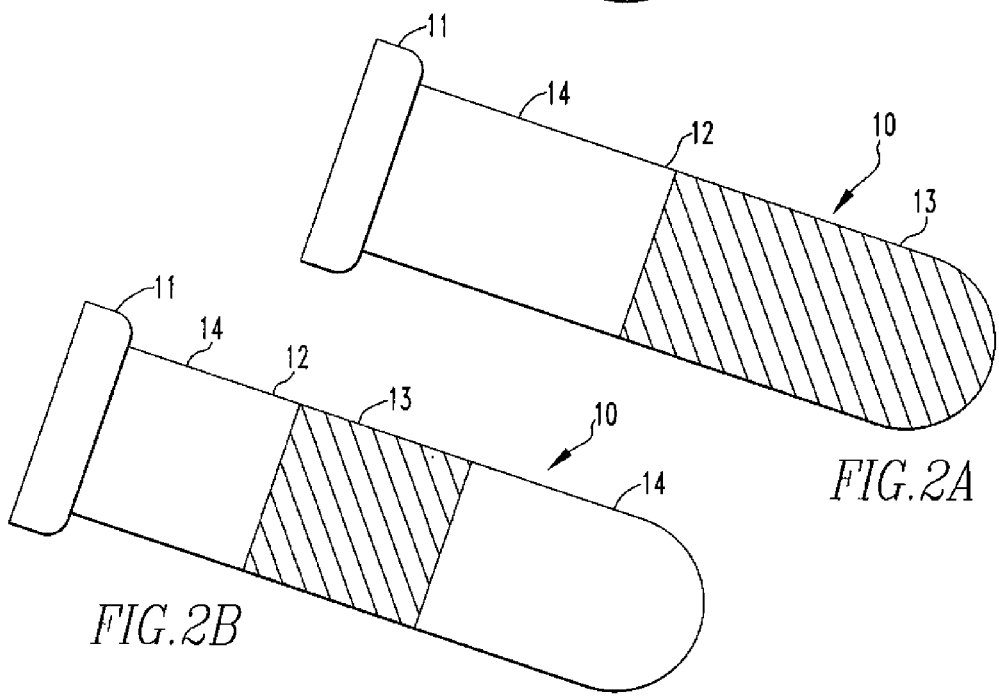
FIG.2A
FIG.2B
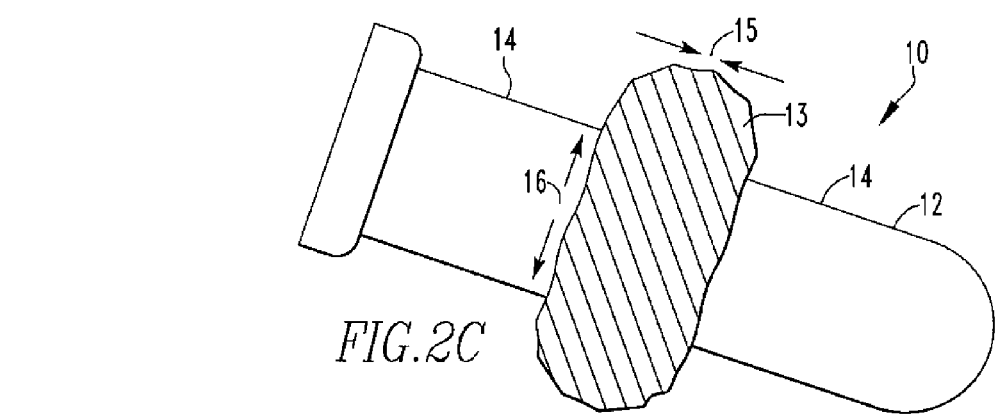
FIG.2C

PROSTHETIC IMPLANTS

CROSS-REFERENCE TO RELATED APPLICATION

This application is a United States National Phase filing of International Application No. PCT/US2008/060458 which claims priority to U.S. Patent Application No. 60/912,694 filed on Apr. 19, 2007. The disclosure of each is incorporated by reference in its entirety.

BACKGROUND

1. Technical Field

The present disclosure relates to prosthetic implants and more specifically, prosthetic implants that include polymer material for fixation of the implant to bone and fixation between implant components.

2. Related Art

During joint replacement surgery, also referred to as replacement arthroplasty, a joint implant is inserted into or otherwise attached to a bone that has been prepared to receive the implant, and the implant is secured. Reliable stabilization, or fixation, is essential for the success of joint replacement. Movement of the implant relative to the bone often results in formation of a fibrous interface between the implant and the bone. The fibrous interface may cause further loosening and, ultimately, destabilization of the implant, thereby necessitating additional surgery or surgeries, commonly referred to as corrective or revision surgeries.

Several methods of fixating joint implants, or components of joint implants, on or in a bone are known. One method of stabilization is to permanently affix the joint implant to the bone using a bone cement. Stabilization with bone cement requires the drilling of oversized holes in the bone, which are filled with the cement prior to insertion of the joint implant. The implant is inserted into the cement-filled bone and allowed to harden. Unfortunately, implants that have been cemented are prone to loosening and are extremely difficult to remove when replacement is required. Furthermore, the cementing process requires difficult preparation of the bone surface.

Other methods of stabilizing a joint implant are cementless methods, which include stabilization by interference or press fit, stabilization by various structures, and other methods. For example, various stabilizing devices or structures, such as pegs, screws, or fins, protrude from the implant and are used to attach the prosthetic joint to the bone. The main disadvantage of this type of cementless method is that the protruding structures frequently create stress patterns in the bone. These stress patterns produce undesirable bone remodeling that can lead to destabilization of the implant. In another type of cementless method, often referred to as biological fixation, the implants are covered, coated, or enveloped with a porous surface material, such as a polymer or a ceramic material that allows bone growth into the surface of the implant. This growth, commonly referred to as "bone ingrowth", stabilizes the implant. While less prone to the destabilization problems encountered when implants are stabilized by other methods, implants stabilized by biological fixation must remain completely secure for three to eight weeks after the implant surgery to allow sufficient bone ingrowth to occur. Any movement of the implant within the bone during these first few weeks after surgery results in the formation of a fibrous interface between the implant and the bone that prevents bone ingrowth and the desired stabilization effect.

When a prosthetic joint deteriorates, loosens, destabilizes, or otherwise becomes problematic, the joint must be removed and replaced with a new joint during a subsequent (or revision) surgery. Stabilization of a new joint implant during a revision surgery is particularly challenging. As a result of the prior removal of large amounts of bone tissue during the first joint replacement surgery, cavities often exist between the new implant and the bone to which the new implant is being attached, thereby making it impossible to achieve a tight fit between the new implant and the bone. It is advantageous to fill these cavities and provide adjunct stabilization of the implant relative to the bone for several reasons. First, undesirable bone remodeling may occur if stress distribution after revision surgery changes. Thus, it is desirable to maintain the load transfer in a bone after revision surgery as similar as possible to that existing with the primary implant. Second, it is desirable to distribute stress patterns in the bone to help bone reconstitution and avoid risk of bone fracture. Third, the filling of cavities helps minimize stress levels in the implant itself, thereby reducing the risk of implant fracture. Additionally, when utilizing a biologically stabilized implant, the cavities should be filled to avoid undesirable movement of the implant relative to the bone, thereby substantially reducing the formation of a fibrous interface to allow proper bone ingrowth and permanent fixation of the implant. Moreover, cavities should be filled to substantially reduce the exposure of unprotected bone tissue. Exposed bone tissue is susceptible to infection and is accessible to harmful polymer particles, which often form as a result of the "shedding" of the polymer-coated, articulating surfaces of joint implants. These polymer particles may cause localized osteolysis, a time-dependent process that arises from an inflammatory reaction caused by the particulate debris of polymer coatings composed of polymers such as polyethylene.

One particularly challenging joint implant stabilization scenario is found in hip replacement revision surgery. During this surgery, the proximal aspect of the femur resembles the shape of an ice cream cone as a result of previous surgeries. Therefore, during revision hip replacement surgery, it is particularly challenging to adjust both the distal and proximal aspects of the femur to fit the implant. When a distally fixed hip implant is installed into a femoral canal, the implant passes through the ice cream cone-shaped proximal aspect of the femur and is secured to a distal aspect of the femur. Due to the shape, a cavity often remains between the implant and the cortical bone tissue in the proximal aspect of the femur. It is desirable to fill the cavity to distribute some of the stress between the distal and proximal femur in order to promote bone reconstitution in the proximal femur. In addition, the filling of the cavity provides additional stabilization of the implant, thereby decreasing the risk of it becoming loose.

Another challenging scenario is an example of hip revision surgery when an acetabulum needs reamed excessively until a substantial portion of it is hemispherical in order to install an acetabular component of a hip prosthesis. Often, achieving a desired shape is still impossible, and a non-optimal bi-lobed configuration of an acetabular component is utilized, such as that in the acetabular components offered by DePuy Orthopaedics (Warsaw, Ind.), or Johnson & Johnson, (New Brunswick, N.J.), or a revision acetabular cage is used. During revision knee replacement arthroplasty, femoral or tibial components are often combined with metal augments, which are wedges or blocks of metal to make up for the lost bone and fill the gaps.

However, the shape of the cavities between a joint implant and a bone is often irregular and cannot be filled by standardized metal implants. To circumvent this problem, the technique of allografting, or packing allograft bone into bone cavities, followed by the introduction of bone cement, is often utilized. The allograft bone is crushed, morselized, or fashioned into shapes suitable for packing the cavity, the shapes are packed into the cavity, and bone cement is added. This allografting technique is prone to all of the problems described above that are associated with cementing methods. Specifically, during any subsequent revision surgeries, removal of the allograft and additional bone tissue is required. This cumulative bone loss creates a natural limit to a number of revisions that can be performed. Restoration of bone tissue, or stock, is limited or does not occur when allografts are used. Moreover, bone necrotization may occur and persist in the allografts.

Morselization of the allograft material may promote bone remodeling and restoration by causing the release of growth factors present in the graft, and the morselized material may be impacted to make it easier for the ingrowing bone to climb up into the graft. However, when allograft bone is being packed into the cavity, significant force is utilized. The use of such force increases risk of bone fracture and trauma. If the allograft material is not morselized, but is fashioned into preformed shapes, the shapes available often do not fit properly into the cavity to be filled. Finally, the use of allografts, in general, carries increased risks of disease transmission and graft rejection. One alternative to allografting is to collapse the adjacent bone around the implant and cable the bone onto the implant. However, this procedure has been associated with bone degradation.

Permanent, such as, metallic fixation devices, must be removed at the time of revision surgery. In the case of screws, there are times when they are difficult to remove, which is time consuming to the surgeon. An added disadvantage is that such devices, particularly screws, may fracture, with the resulting remnants causing tissue damage. Also available are spikes, pegs, or fins, or any combination thereof, that are driven into the bone, for example, for fixation around the periphery or the dome of acetabular cups, however, upon their removal, a hole or cavity is formed that still must be filled with bone graft during revision surgery.

A modular peg is currently available for fixation of an acetabular component of a hip implant. The modular peg can be inserted for fixation after the acetabular cup was implanted. Due to it being broad compared to the root diameter of a screw, the peg provides better rotational stability than the screw. Moreover, the peg seals a connection between the acetabular cup and the peg, thereby substantially reducing exit of debris through this connection. During revision surgery, the peg can be removed prior to removal of the cup, which allows curved osteotomies, or gouges, to be passed around the outside of the acetabular shell during surgery, thus simplifying the procedure. Still, the modular peg results in a cavity in an acetabular bed that requires packing with bone graft or other materials.

Temporary fixation structures manufactured of resorbable, degradable, or temporary, materials are gradually resorbed by the tissue after the installation. The resulting bone cavity is gradually replaced by re-growing bone. A variety of biodegradable devices for temporary fixation of joint implants are available, all of which, however, suffer from a variety of shortcomings. Bone screws manufactured of materials that are resorbed by the body are available. While they do not require removal after the need for fixation passes, they are of limited mechanical strength. When bone screws are used for fixation of an acetabular component of a hip implant, fixation is often lost prematurely, thus not allowing adequate time for the bone ingrowth to occur, and resulting in destabilization of the implant on the bone. In general, bone screws, including those made of resorbable materials, are known to back out of the bone, press against polymer components of a joint implant, create dents, and generate polymer particles. Moreover, degradation, or resorption of the screw material occurs faster than bone re-growth, thus leaving exposed cavity, which is also prone to osteolysis, particularly in the cases where polymeric prosthetic surfaces are employed that may generate particles during operation of the prosthesis. Generally, a challenge is to adjust the rate of degradation of such a temporary fixation device to correspond to the rate of bone tissue regrowth, thereby substantially reducing the presence of a bone cavity, or exposed bone tissue, prone to infection or osteolysis. Covers, or seals, to cover screw holes in the bone, are available, however, these require additional fitting and installation steps during surgery.

In general, many of the currently available methods and devices for adjunct stabilization of implants, such as impaction allografting or the collapsing and cabling of bone, require the presence of sufficient amounts of high quality bone tissue in the bone to which the implant is being attached. When bone tissue is lost, due to disease or a pathological condition or for other reasons, the constructs become unstable. Persons with thin or fragile bones, such as osteoporosis patients, avascular necrosis patients, and patients with metastatic bones, are especially in need of joint implants. However, their bone tissue is often not sufficiently strong for the stabilization of joint implants without adjunct fixation. Therefore, currently available adjunct stabilization devices and methods fail to satisfy the requirements of patients who are most in need of joint implants.

Thus, there is a need for systems and devices that provide reliable adjunct stabilization of joint implants yet allow for reestablishment of bone, bone ingrowth, or restoration of bone stock. Particularly, there is a need for methods that provide additional stabilization of implants in tubular bones. Specifically, implants are needed that permit and promote bone regrowth in the cavities between the implant and the bone cortex. This need is particularly urgent during revision arthroplasties, such as revision hip replacement arthroplasty, when a large amount of bone tissue has been removed during prior surgeries and it particularly challenging to tightly fit an implant into a bone without leaving a bone cavity, or in situations when disease and pathological conditions reduce the amount and quality of bone tissue available for fitting.

Devices and systems for adjunct stabilization are needed that allow for bone restoration, are easily adaptable to a variety of local conditions, reliably stabilize the implant, maintain the load transfer, and distribute stress patterns in the bone in a manner that promotes bone reconstitution, reduces the risk of bone fracture, reduces stress levels in the implant itself, and reduces the risk of implant fracture. Suitable devices and systems are needed that generally reduce undesirable movement of the implant relative to the bone for a required period of time, thereby substantially reducing formation of a fibrous tissue at the bone-implant interface. There is a particular need to temporarily and reliably stabilize uncemented joint implants to allow for bone ingrowth to occur on the surface of the implant and permanently stabilize the implant on the bone. At the same time, the devices and structures for adjunct stabilization are needed that would allow foregoing additional surgical procedures necessary to remove the devices from the body once the need in the stabilization, or fixation, passes, and, preferably, would allow substantially reducing the removal of the temporary fixation devices and structures during any required revision surgeries altogether, thus avoiding the risks of tissue damage associated with such removal and other surgical complications.

Moreover, systems and devices are needed that protect exposed bone tissue from undesired contact with particles and infectious agents after installation of the implant, thereby reducing the risks of infection and osteolysis. Additionally, devices and systems are needed that are sufficiently inert and stable in the human body, possess adequate mechanical and chemical properties to stabilize a joint implant in tissues and reliably remain in the tissues without causing undesirable side effects, such as degradation, undesired bone or soft tissue redistribution, or mechanical damage. The needed devices and systems should also provide adequate stabilization for a sufficient period of time to allow bone ingrowth to occur. Also desirable are systems that can serve as carriers for advantageous biologically active molecules, such as growth factors or antibiotics.

Also, stabilization devices and systems are desired that simplify removal of the implant during any required subsequent revision surgeries, thereby decreasing bone degradation and the risks of tissue damage associated with such removal, as well as other surgical complications. In general, temporary fixation devices and systems are needed that are readily available to a surgeon, easy to use, minimize tissue damage, and simplify any subsequently required surgical procedures. Temporary fixation devices and systems are needed that are versatile, allow for faster healing with fewer complications, require less immobilization, are easy to use and manufacture, and are inexpensive to produce and operate.

SUMMARY

In one aspect, the present disclosure relates to a device, which may be an elongated member, for stabilization of a prosthetic implant in bone tissue. The device includes at least one resorbable component and at least one non-resorbable component. The resorbable component includes a polymer material having shape memory qualities and is selected from a group including an amorphous polymer, a semi-crystalline polymer, and combinations thereof. The non-resorbable component is selected from a group including a metal material, a non-metal material, and combinations thereof. The implant is selected from a group including a hip implant, a knee implant, a shoulder implant, and an elbow implant. In an embodiment, the resorbable component includes alternating sections of a polymer material having shape memory qualities and a polymer material that does not have shape memory qualities. In another embodiment, the device includes a peg having a locking shoulder portion and a peg portion, wherein the non-resorbable component is the locking shoulder portion and the resorbable component is the peg portion.

In another aspect, the present disclosure relates to a prosthetic implant. The prosthetic implant includes a body having an outer surface, an inner surface, and at least one device for fixating the implant to bone tissue. The device includes at least one resorbable component and at least one non-resorbable component. The resorbable component includes a polymer material having shape memory qualities and the device is coupled to the outer surface of the body.

In yet another aspect, the present disclosure relates to a method of stabilizing a prosthetic implant. The method includes inserting the implant, which may include openings, into a body of a human or animal; providing a device for stabilization of the implant; inserting the device through the openings and into a bone tissue of the human or animal; and causing the polymer material to deform, wherein causing the polymer material to deform fixates the device to the bone tissue and causes stabilization of the implant. The device includes at least one resorbable component and at least one non-resorbable component. The resorbable component includes a polymer material having shape memory qualities.

In a further aspect, the present disclosure relates to a method of fixating a prosthetic implant to bone. The method includes providing a prosthetic implant that includes a body having an outer surface, wherein the outer surface includes at least one device for fixating the implant to bone, the device including at least one resorbable component and at least one non-resorbable component, the resorbable component including a polymer material having shape memory qualities; inserting the device into the bone; and causing the polymer material to deform, wherein causing the polymer material to deform fixates the device to the bone and causes fixation of the implant to the bone.

In yet a further aspect, the present disclosure relates to a prosthetic implant that includes a body having an outer surface and a coating located on the outer surface of the body. The coating includes a polymer material having shape memory qualities.

In yet an even further aspect, the present disclosure relates to a method of fixating a prosthetic implant to bone tissue. The method includes providing a prosthetic implant having a body with an outer surface and a coating, that includes a polymer material having shape memory qualities, located on the outer surface of the body; inserting the implant into the bone tissue; and causing the polymer material to deform to fixate the implant to the bone tissue.

In another aspect, the present disclosure relates to a liner for use with a prosthetic implant. The liner includes an outer surface and an inner surface. The outer surface includes at least one device for fixating the liner to the implant. The device includes a resorbable component including a polymer material having shape memory qualities.

In yet another aspect, the present disclosure relates to a liner for use with a prosthetic implant. The liner includes an outer surface and an inner surface. The outer surface includes an indentation, wherein a polymer material is located within the indentation. The polymer material includes shape memory qualities.

In yet a further aspect, the present disclosure relates to a liner for use with a prosthetic implant. The liner includes an outer surface and an inner surface. The liner includes alternating sections of a polymer material having shape memory qualities and a polymer material that does not have shape memory qualities.

In another aspect, the present disclosure relates to a prosthetic implant that includes a body having an outer surface and an inner surface, wherein the outer surface includes at least one opening. A liner is coupled to the inner surface of the body and includes an outer surface and an inner surface, wherein the outer surface includes at least one device for fixating the liner to the implant. The device, which extends through the opening, includes a resorbable component. The resorbable component includes a polymer material having shape memory qualities.

In yet another aspect, the present disclosure relates to a prosthetic implant that includes a body having an outer surface and an inner surface and a liner coupled to the inner surface of the body. The liner includes an outer surface having an indentation and a polymer material located within the indentation. The polymer material includes shape memory qualities.

In a further aspect, the present disclosure relates to a prosthetic implant that includes a body, having an outer surface and an inner surface, and a liner coupled to the inner surface of the body. The liner, which includes an outer surface and an inner surface, also includes alternating sections of a polymer material having shape memory qualities and a polymer material that does not have shape memory qualities.

In an even further aspect, the present disclosure relates to a method of fixating an acetabular liner to an acetabular shell of a hip implant. The method includes providing an acetabular shell having a body including an outer surface and an inner surface, wherein the outer surface includes at least one opening; providing an acetabular liner that includes an outer surface and an inner surface, the outer surface including at least one device for fixating the liner to the implant, the device including a resorbable component including a polymer material having shape memory qualities; locating the acetabular liner within the acetabular shell such that the device on the outer surface of the acetabular liner is inserted into the opening of the acetabular shell; and causing the polymer material to deform to fixate the acetabular liner to the acetabular shell.

In yet an even further aspect, the present disclosure relates to a method of fixating an acetabular liner to an acetabular shell of a hip implant. The method includes providing an acetabular shell having a body including an outer surface and an inner surface; providing an acetabular liner, the liner including an outer surface and an inner surface, the outer surface having an indentation and a shape memory polymer material, having shape memory qualities, located within the indentation; locating the acetabular liner within the acetabular shell such that the inner surface of the acetabular shell covers the outer surface of the liner; and causing the polymer material to deform to fixate the acetabular liner to the acetabular shell.

In another aspect, the present disclosure relates to a method of fixating an acetabular liner to an acetabular shell of a hip implant. The method includes providing an acetabular shell having a body including an outer surface and an inner surface; providing an acetabular liner, the liner including an outer surface and an inner surface, wherein the liner includes alternating sections of a polymer material having shape memory qualities and a polymer material that does not have shape memory qualities; locating the acetabular liner within the acetabular shell such that the inner surface of the acetabular shell covers the outer surface of the acetabular liner; and causing the polymer material having shape memory qualities to deform to fixate the acetabular liner to the acetabular shell.

In yet another aspect, the present disclosure relates to a head for use on an intramedullary implant. The head includes an outer surface, an inner surface, and alternating sections of a polymer having shape memory qualities and a polymer that does not have shape memory qualities.

In a further aspect, the present disclosure relates to a head for use on an intramedullary implant. The head includes an outer surface and an inner surface. The inner surface includes an indentation and a polymer material located within the indentation. The polymer material including shape memory qualities.

In an even further aspect, the present disclosure relates to an intramedullary implant including a shaft, a neck, and a head coupled to the neck. The head includes an outer surface, an inner surface, and alternating sections of a polymer material having shape memory qualities and a polymer material that does not have shape memory qualities. In an embodiment, the implant further includes a shape memory polymer material coupled to the neck.

In yet an even further aspect, the present disclosure relates to an intramedullary implant including a shaft, a neck, and a head coupled to the neck. The head includes an outer surface and an inner surface, wherein the inner surface includes an indentation and a polymer material located within the indentation. The polymer material includes shape memory qualities. In an embodiment, the implant further includes a shape memory polymer material coupled to the neck.

In another aspect, the present disclosure relates to a method of fixating a femoral head to a femoral implant. The method includes providing a femoral implant including a shaft and a neck; providing a femoral head, the head including an outer surface and an inner surface, wherein the head includes alternating sections of a polymer material having shape memory qualities and a polymer material that does not have shape memory qualities; placing the femoral head over the neck of the femoral implant such that the inner surface of the head covers an outer surface of the neck; and causing the polymer material having shape memory qualities to deform to fixate the head to the neck. In an embodiment, the method further includes a polymer material coupled to the neck, the polymer material including shape memory qualities. In another embodiment, the method further includes causing the polymer material to deform to fixate the femoral head to the neck.

In yet another aspect, the present disclosure relates to a method of fixating a femoral head to a femoral implant. The method includes providing a femoral implant including a shaft and a neck; providing a femoral head; the head including an outer surface, and an inner surface, the inner surface including an indentation, and a polymer material located within the indentation, the polymer material having shape memory qualities; placing the femoral head over the neck of the femoral implant such that the inner surface of the head covers an outer surface of the neck; and causing the polymer material to deform to fixate the head to the neck. In an embodiment, the method further includes a polymer material coupled to the neck. The polymer material includes shape memory qualities. In an embodiment, the method further includes causing the polymer material to deform to fixate the femoral head to the neck In a further aspect, the present disclosure includes an intramedullary implant including a shaft, the shaft including a polymer material coupled to the shaft, and a neck. In another embodiment, the shaft includes at least one groove, multiple grooves, screw threads, circumferential ribs, or at least one engraving. In another embodiment, the shaft includes a porous surface. The polymer material, which may be either resorbable or non-resorbable, includes shape memory qualities and is selected from a group consisting essentially of an amorphous polymer, a semi-crystalline polymer, and combinations thereof. The implant comprises a metal material selected from a group including titanium, titanium alloys, steel, stainless steel, cobalt-chromium alloys, tantalum, magnesium, niobium, nickel, nitinol, platinum, silver, zirconium, and combinations thereof.

In yet another aspect, the present disclosure relates to a method of fixating an intramedullary implant to a bone. The method includes providing an intramedullary implant including a shaft, the shaft having a polymer material coupled to the shaft, and a neck; inserting the intramedullary implant into a bone; and causing the polymer material to deform, wherein causing the polymer material to deform fixates the intramedullary implant to the bone.

In another aspect, the present disclosure relates to a sleeve body for use with an intramedullary implant. The sleeve includes an outer portion and an inner portion, the outer portion having a polymer material coupled to the outer portion. In an embodiment, the sleeve body further includes a polymer material coupled to a wall of the inner portion. In another embodiment, the polymer material includes shape memory qualities.

In yet another aspect, the present disclosure relates to an intramedullary implant that includes a shaft, a neck, and a sleeve body coupled to the shaft, the sleeve body including an outer portion, the outer portion including a polymer material coupled to the outer portion, and an inner portion, the inner portion covering at least a segment of the shaft. In an embodiment, the intramedullary implant further includes a polymer material coupled to a wall of the inner portion of the sleeve. In another embodiment, the polymer material includes shape memory qualities.

In a further aspect, the present disclosure relates to a method of fixating a sleeve body to an intramedullary implant. The method includes providing an intramedullary implant having a shaft and a neck; providing a sleeve body, the sleeve body including an outer portion and an inner portion, the inner portion comprising a polymer material coupled to a wall of the inner portion; locating the sleeve body on the shaft such that the inner portion of the sleeve body covers at least a segment of the shaft; and causing the polymer material to deform to fixate the sleeve body to the shaft.

In yet a further aspect, the present disclosure relates to a method of fixating an intramedullary implant to a bone. The method includes providing an intramedullary implant having a shaft, a neck, and a sleeve body coupled to the shaft, the sleeve body including an outer portion and an inner portion, the outer portion including a polymer material coupled to the outer portion, the inner portion covering at least a segment of the shaft; inserting the intramedullary implant into a bone; and causing the polymer material to deform to fixate the intramedullary implant to the bone.

In an even further aspect, the present disclosure relates to a hip implant including a shell, the shell comprising an outer portion and an inner portion, and a stem comprising a resorbable shape memory polymer material, the stem coupled to the inner portion of the shell. In an embodiment, the stem includes alternating sections of a shape memory polymer material and a non-shape memory polymer material, the shape memory polymer material and the non-shape memory polymer material both being resorbable.

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the present disclosure. In the drawings:

FIG. 1 shows a perspective view of a device of the present disclosure for stabilization of a prosthetic implant in bone tissue.

FIGS. 2A and 2B show perspective views of the device in FIG. 1 having resorbable components that include alternating sections of polymer material having shape memory qualities and polymer material not having shape memory qualities.

FIG. 2C shows a perspective view of the device in FIG. 2B after deformation of the shape memory polymer material.

DETAILED DESCRIPTION OF THE EMBODIMENTS

Figure 3A:
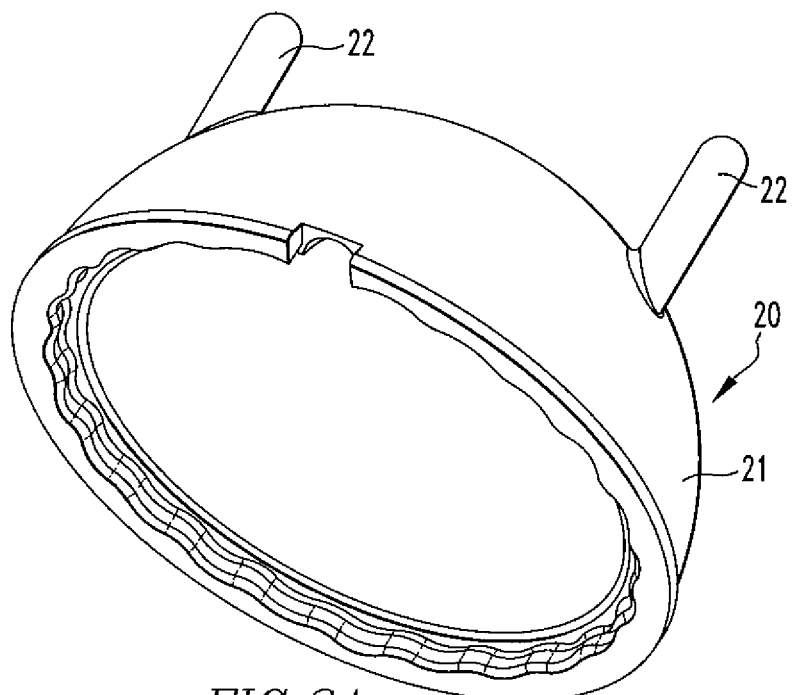
FIGS. 3A and 3B show perspective views of a prosthetic implant of the present disclosure before and after deformation of the resorbable devices, respectively.

The following description of the preferred embodiment(s) is merely exemplary in nature and is in no way intended to limit the present disclosure, its application, or uses.

In one aspect, the present disclosure relates to elongated members, such as pegs or fins, which include at least one resorbable component and at least one non-resorbable component. During implantation of a prosthetic implant, the resorbable component is inserted into a bone and deformed to fixate the prosthetic implant to the bone. The resorbable component is gradually resorbed into the bone after surgical insertion of the implant. The resorption period is such that adequate fixation is provided for a period of time necessary for bone ingrowth to occur after which period the fixation provided by the resorbable device is no longer needed.

Examples of the device are shown in FIGS. 1, 2A, and 2B. The peg 10 includes a shoulder portion 11 including a non-resorbable component, which is responsible for maintaining a water-tight seal once a peg is inserted into the bone, and a resorbable peg portion 12, for maintaining fixation for a required period of time after insertion into the bone. The non-resorbable component 11 is selected from a group that includes a metal material, a non-metal material, or combinations thereof. For the purposes of FIG. 1, the resorbable component 12 includes a polymer material having shape memory qualities. For the purposes of FIGS. 2A and 2B, the resorbable portion 12 includes alternating sections of a polymer material having shape memory qualities 13 and a polymer material that does not have shape memory qualities 14. In both cases, the resorbable component 12 is provided with energy, after insertion of the component 12 into the bone, to deform the polymer material having shape memory qualities and fixate the prosthetic implant to bone.

As shown in FIG. 2C, deformation of the shape memory polymer material may result in a section 13 shrinking axially 15, or along the length of the section 13, and expanding radially 16, or along the width of the section 13. However, for the purposes of this disclosure, deformation of the component 12 is not limited to an increase in width and a decrease in length. Rather, other types of deformation may occur. For example, the component 12 may bend, but not necessarily increase in width. Factors that determine the type of deformation include, but are not limited to, material, mold design, and mold conditions.

Both the shape memory polymer material and the non shape memory polymer material include an orientated resorbable material and are selected from a group that includes an amorphous polymer, a semi-crystalline polymer, or a composition having a combination thereof. Factors used to determine the type of shape memory polymer used, include, but are not limited to, the desired amount of polymer deformation, the desired rate at which that deformation occurs, the rate at which the polymer is absorbed, and the strength of the polymer.

The shape memory polymer material is processed to have shape memory qualities and therefore changes shape or deforms, as stated above, by shrinking axially, or along the length of the material, and expanding radially, or along the width of the material. This expansion and shrinkage causes an interference fit between the polymer material and the bone, thereby fixating the prosthetic implant to the bone.

Generally, polymers that display shape memory qualities show a large change in modulus of elasticity at the glass transition temperature ($T_g$). The shape-memory function can be achieved by taking advantage of this characteristic. Namely, a molded article (primary molded article) to which a definite shape (the original shape) has been imparted by a common method for molding plastics, is softened by providing the article with energy and heating to a temperature ($T_f$) higher than the $T_g$ of the polymer, but lower than the melting temperature ($T_m$) thereof so as to deform it into a different shape. Next, the molded article is cooled to a temperature lower than the $T_g$, while maintaining the thus deformed shape (secondary molded article). When it is heated again to a temperature higher than the secondary molding temperature $T_f$, but lower than the $T_m$, the shape of the secondary molded article disappears and thus the article is recovered to the original shape of the primary molded article. In addition, the change in shape of the material during deformation can be tailored depending on the mode of deformation For the purposes of this disclosure, a molded article (i.e. the above-mentioned resorbable component), having a definite shape (original shape) is formed, or sections of it are formed, from shape memory polymer material and is provided with energy to heat the component or section to a temperature above the glass transition temperature of the polymer, but lower than the melting temperature ($T_m$) thereof so as to deform it into a different shape and effectively wedge the component or section between the prosthetic implant and the bone. In this manner, the prosthetic implant becomes fixed to the bone. However, rather than cooling the component and heating it again until it recovers its original shape, the component is kept in this deformed shape so as to maintain fixation of the implant to the bone. The glass transition temperature of the polymer material will vary based on a variety of factors, such as molecular weight, composition, structure of the polymer, and other factors known to one of ordinary skill in the art. In addition, the change in shape of the material during deformation can be tailored depending on the mode of deformation whether this is uniaxial, biaxial, triaxial, or under tension, compression, or shear.

Examples of adding energy to heat the shape memory polymer material include electrical and or thermal energy sources. It is also within the scope of this disclosure that once the component is placed in the bone, body heat would be transferred from blood and tissue, via thermal conduction, to provide the energy necessary to deform the shape memory polymer material. In this instance, body temperature would be used as the thermal energy source. Furthermore, the shape memory polymer material could be deformed via other methods known to those of ordinary skill in the art, including, but not limited to, the use of force, or mechanical energy, a solvent, and/or a magnetic field. Any suitable force that can be applied either preoperatively or intra-operatively can be used. One example includes the use of ultrasonic devices, which can deform the polymer material with minimal heat generation. Solvents that could be used include organic-based solvents and aqueous-based solvents, including body fluids. Care should be taken that the selected solvent is not contra indicated for the patient, particularly when the solvent is used intra-operatively. The choice of solvents will also be selected based upon the material to be deformed. Examples of solvents that can be used to deform the shape memory polymer material include alcohols; glycols, glycol ethers, oils, fatty acids, acetates, acetylenes, ketones, aromatic hydrocarbon solvents, and chlorinated solvents. Finally, the shape memory polymer material could include magnetic particles and deformation could be initiated by inductive heating of the magnetic particles through the use of a magnetic field.

Specific polymers that may be used for the component, or sections of the component, include polyetheretherketone (PEEK), polymethyl methacrylate (PMMA), polyethyl methacrylate (PEMA), polyacrylate, poly-alpha-hydroxy acids, polycapropactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof. In addition, bioactive agents may be incorporated into both the shape memory polymer material and the non-shape memory polymer material, to be released during the deformation or the degradation of these polymer materials. These agents are included to help promote bone regrowth. Examples include bone morphogenic proteins, antibiotics, anti-inflamatories, angiogenic factors, osteogenic factors, monobutyrin, omental extracts, thrombin, modified proteins, platelet rich plasma/solution, platelet poor plasma/solution, bone marrow aspirate, and any cells sourced from flora or fawna, such as living cells, preserved cells, dormant cells, and dead cells. Other bioactive agents known to one of ordinary skill in the art may also be used. Furthermore, the polymeric materials can be formed as a composite or matrix and include reinforcing material or phases such as fibers, rods, platelets, and fillers. For example, the polymeric material can include glass fibers, carbon fibers, polymeric fibers, ceramic fibers, or ceramic particulates. Other reinforcing material or phases known to one of ordinary skill in the art could also be used.

In certain embodiments, the device is ultrasonically welded, molded, heat pressed, by heating a resorbable component, a permanent component, or both, or otherwise attached, for example, by mechanical means, to a surface of a prosthetic implant, including but not limited to a tibial or a femoral component of a knee prosthetic implant, a glenoid component of a shoulder implant, or an acetabular cup component of a hip implant. The prosthetic implant stabilized with the devices comprises openings through which the fixation devices are inserted during surgery. For the purposes of this disclosure, the non-resorbable component of the fixation device is a metallic piece, which, upon insertion of the device through the opening, into the prosthetic implant, and into the bone, is flush with the surface of the prosthetic implant, being securely anchored to the opening and the surface of the prosthetic implant.

Figure 3B:
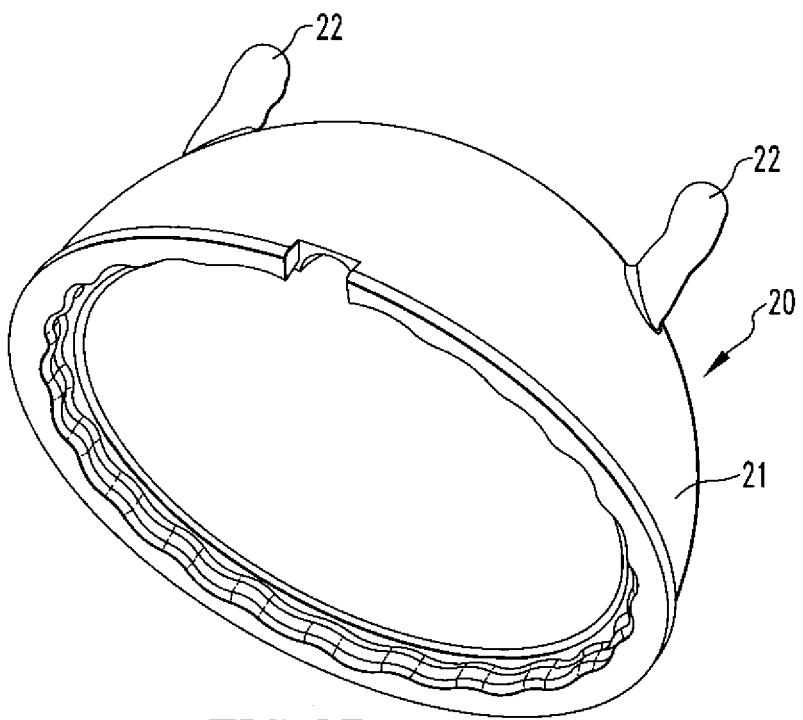

In one embodiment, a polymeric peg or fin or adjunct fixation devices is ultrasonically welded to the surface of an acetabular cup, glenoid, tibial or femoral component. In FIGS. 3A and 3B, a prosthetic device, specifically an acetabular cup 20 with a metal shell 21 and resorbable pegs 22, is schematically represented. The pegs 22 are secured to the metal shell 21. The pegs 22 may be the pegs that are shown in FIGS. 1 and 2A-2C and described above. The acetabular cup 20 is implanted by a method of implantation similar to conventional current surgical techniques and the pegs 22 are then provided with energy to deform the pegs 22, as shown in FIG. 3B, and fixate the acetabular cup 20 to the bone. A resorbable material of the resorbable component begins to loose its mechanical properties several months after implantation, or whenever the need for fixation from the pegs is no longer is necessary. Should revision surgery ever be necessary, the resorbable pegs would not adversely affect the ability of a surgeon, during revision surgery, to remove the prosthetic device, as, by this time, bone, at least partially, fills the spaces left by the resorbable material, unlike when conventional metal spikes are used.

In another variation, a prosthetic implant in which holes, or openings, are present, such as those for metallic anchoring devices, is modified so that the nonresorbable component of the device, such as a metallic piece component, is designed and manufactured to be inserted into the opening, or function as the opening's cover, and is securely anchored to the shell, tibial plateau or glenoid component of the implant, thereby integrating the resorbable component into the cover.

In a method of use of a device according to this present disclosure, an acetabular component of a hip implant, including a screw opening, is inserted according to a method that includes: creating an initial cavity, installing the acetabular component, and inserting the device through the screw opening in the acetabular component until the resorbable component is fully seated in a bone. The non-resorbable component of the device is securely attached to the acetabular shell. This method is not limited to installation of acetabular components of hip implants, but is also used for tibial components, acetabular components, or any implants, where there is a hole, or an opening, or need for adjunct stabilization, or fixation.

Other variations on the devices according to the present disclosure include, but are not limited to, various fixation, or stabilization devices, such as, but not limited to, those similar to a "pop rivet", drywall mounting screw, a Richards Flex Lock Peg, etc. In situations of revision surgery, devices can be manufactured that include relatively large amounts of a resorbable material.

In another non-limiting variation, such as in a case of an acetabular revision surgery, the surgeon can modify a shape of the device with a suitable instrument, such as a powered burr, or other surgical instrumentation, so that the device is shaped to fit a particular application, or a patient's bone defect, with a goal that, in time, the resorbable material is replaced with the bone.

In one more non-limiting variation, the device includes polymer materials with different resorption rates. For example, the resorbable component may be partitioned into three different zones. The most distal zone would comprise a resorbable material with the shortest resorption time of the three zones. The next proximal zone would comprise a resorbable material that would be resorbed the next fastest, and, finally, the most proximal zone would comprise a material with a slowest rate of resorption. As the resorption takes place, the load transfer to the femur from the implant occurs more proximally, and stresses, or loads, the bone more, thereby aiding in bone growth, or remodeling. As a result, the proximal femur maintains superior bone mass.

A metal core can be utilized in certain variations of the devices, thereby providing at least two advantages to the device: first, minimization of the mechanical strength that would be required from a resorbable material of the device, and, second, reduction in the amount of a mass of a resorbable material for resorption by the body of a human or an animal.

It is to be understood that the use of the resorbable adjunct stabilization devices according to aspects and embodiments of the present disclosure is not limited to installation of a hip implant during revision surgery, as described above, but includes use during any joint replacement surgery. The use of the devices and methods for stabilization of prosthetic implants of bones and joints, including but not limited to hip, knee, shoulder, elbow, ankle, wrist, finger joint or toe joint, jaw, skull or spinal prostheses, further including, but not limited to, femoral head implants, femoral stem implants, acetabular cup implants, hinged knee implants, tibial, femoral, or meniscal components of knee implants, patella implants, humeral, glenoid, or ulnar components of prosthetic shoulder or elbow implants, is envisioned and falls within the scope of the present disclosure.

Also falling within the scope of the present disclosure is the use of the devices and methods according to aspects and embodiments of the present disclosure for treatment of various bone and joint diseases and pathological conditions, particularly in, but not limited to, disease and pathological conditions that reduce the amount and quality of bone tissue available for fitting, such as arthritis, including osteoarthritis and rheumatoid arthritis, arthropathy, avascular necrosis, cancer and metastases, tuberculosis, osteoporosis, trauma, such as fractures and dislocations, deformities, including but not limited to, birth defects and genetic anomalies, infections, such as tuberculosis, bone neoplasms, osteitis deformans, osteochondritis, osteonecrosis, bone demineralization, or any combination or variation thereof, or condition related thereto.

Use of the systems, devices, and methods for stabilization of cemented or cementless joint implants, including the joint implants stabilized by biological stabilization, is also envisioned and included within the scope of the present disclosure. In general, the scope of the present disclosure includes use of the methods, devices, and systems described herein in any method of repair or attachment of bones and other tissues, such as connective tissue, including, but not limited to, bone, loose connective tissue, fibrous connective tissue, such as that found in ligaments and tendons, cartilage and adipose tissue, endothelial tissue, epithelial tissue, glandular tissue, muscle tissue, or any artificial, semi-artificial, or engineered tissue. Generally, the resorbable devices of the present invention are used wherever temporary stabilization of tissues and filling of cavities is advantageous.

Figure 4A:
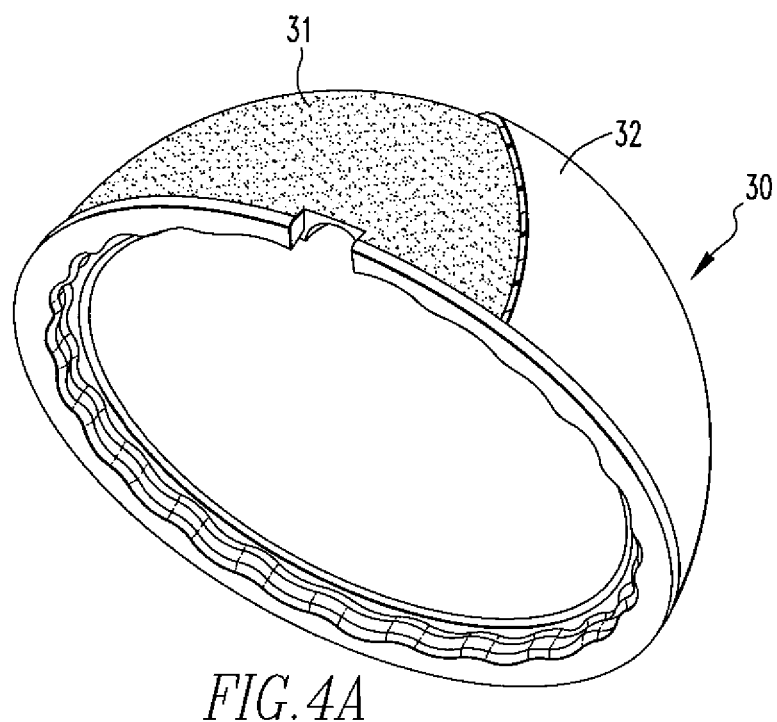
FIGS. 4A and 4B show perspective views of another prosthetic implant of the present disclosure before and after deformation of the polymeric coating on the outer surface of the implant.
Figure 4B:
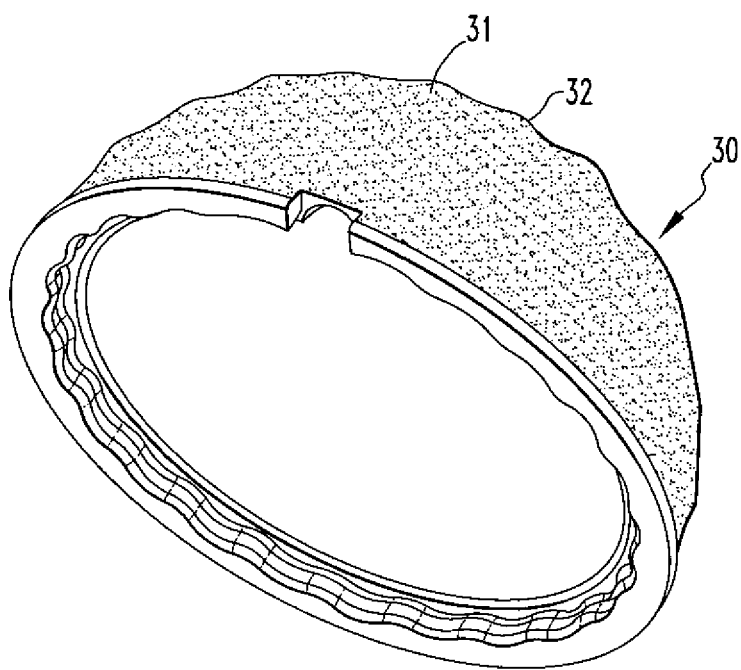

Rather than using devices, such as pegs, to fixate the prosthetic implant, such as an acetabular cup, to bone, the outer surface 31 of the cup 30 may be covered with a resorbable, shape memory polymer material 32, as shown in FIG. 4A, that deforms, or expands, upon the application of energy to the material 32, as shown in FIG. 4B. Upon expansion, an interference fit is created between the polymer material 32 and the bone to fixate the prosthetic implant, or acetabular cup 30, to the bone. The outer surface 31 of the cup 30 is porous to allow for in-growth of bone as the material 32 is resorbed into the body.

Figure 5:
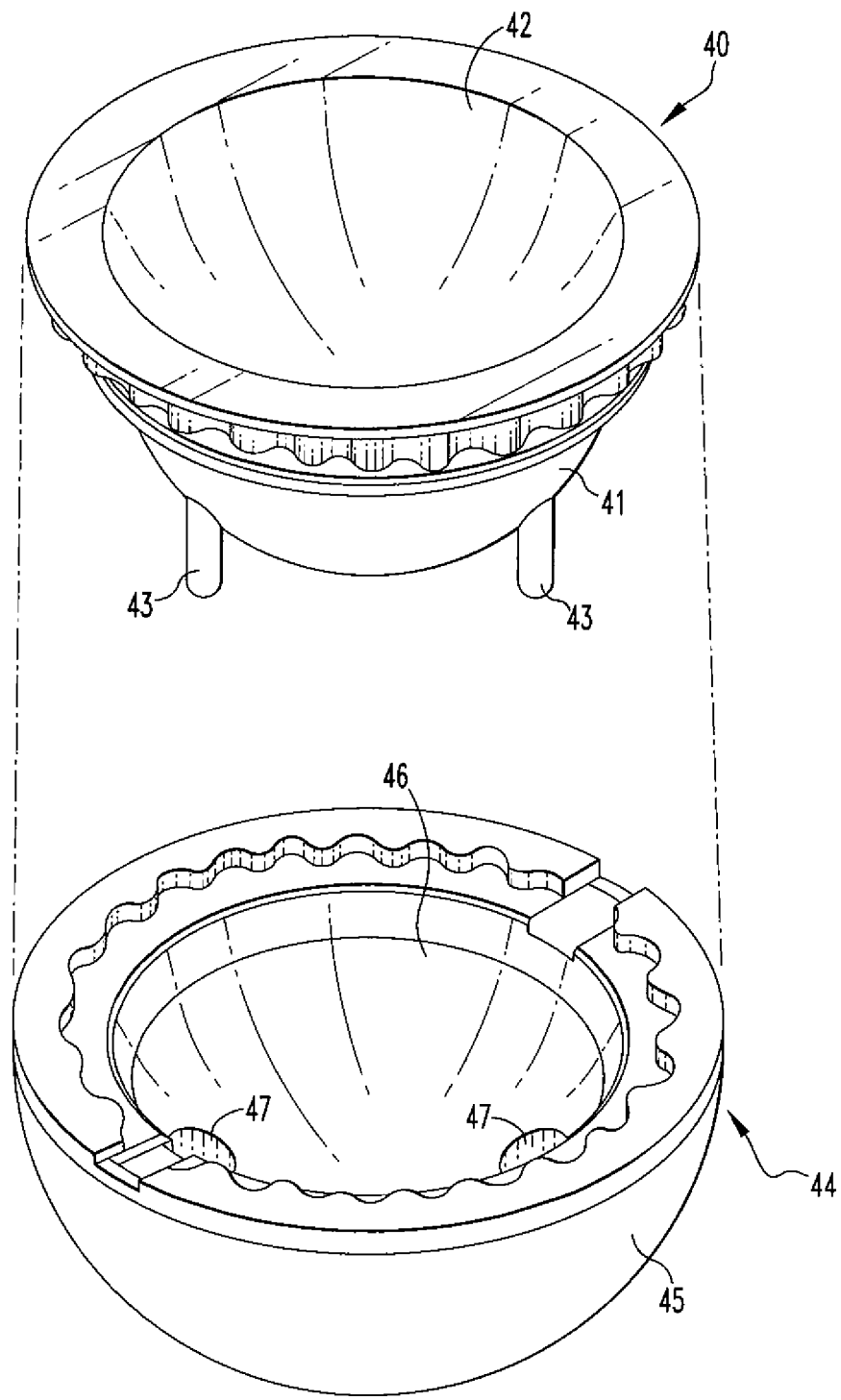
FIG. 5 shows a perspective view of a first embodiment of a liner/prosthetic implant combination of the present disclosure.

In another aspect, the present disclosure relates to a liner for use with a prosthetic implant. Shown in FIG. 5 is an acetabular liner 40 that includes an outer surface 41 and an inner surface 42. The liner 40 includes polymeric devices 43, or pegs, similar to the devices shown in FIGS. 1 and 2A-2C. However, the polymeric devices 43 in FIG. 5 are completely resorbable, rather than having a non-resorbable component and a resorbable component. The devices 43 may be made entirely out of a shape memory polymer material or have alternating sections of shape memory polymer material and non shape memory polymer material. Also shown in FIG. 5 is an acetabular cup 44 that includes an outer surface 45, an inner surface 46, and openings 47 on the outer surface 45 that extend through to the inner surface 46. In a particular embodiment, the liner 40 is inserted into the inner surface 46 of the cup 44 such that the pegs 43 are located within the openings 47 of the cup 44. The pegs 43 may then be provided with energy to deform the pegs 43 and fixate the liner 40 to the cup 44. In another embodiment, the cup/liner combination may be inserted into the body of a human or animal, such that the pegs 43 are inserted into the bone, and then the pegs 43 may be provided with energy to deform the pegs 43 and, not only fixate the liner 40 to the cup 44, but also fixate the cup 44 to the bone.

Figure 6:
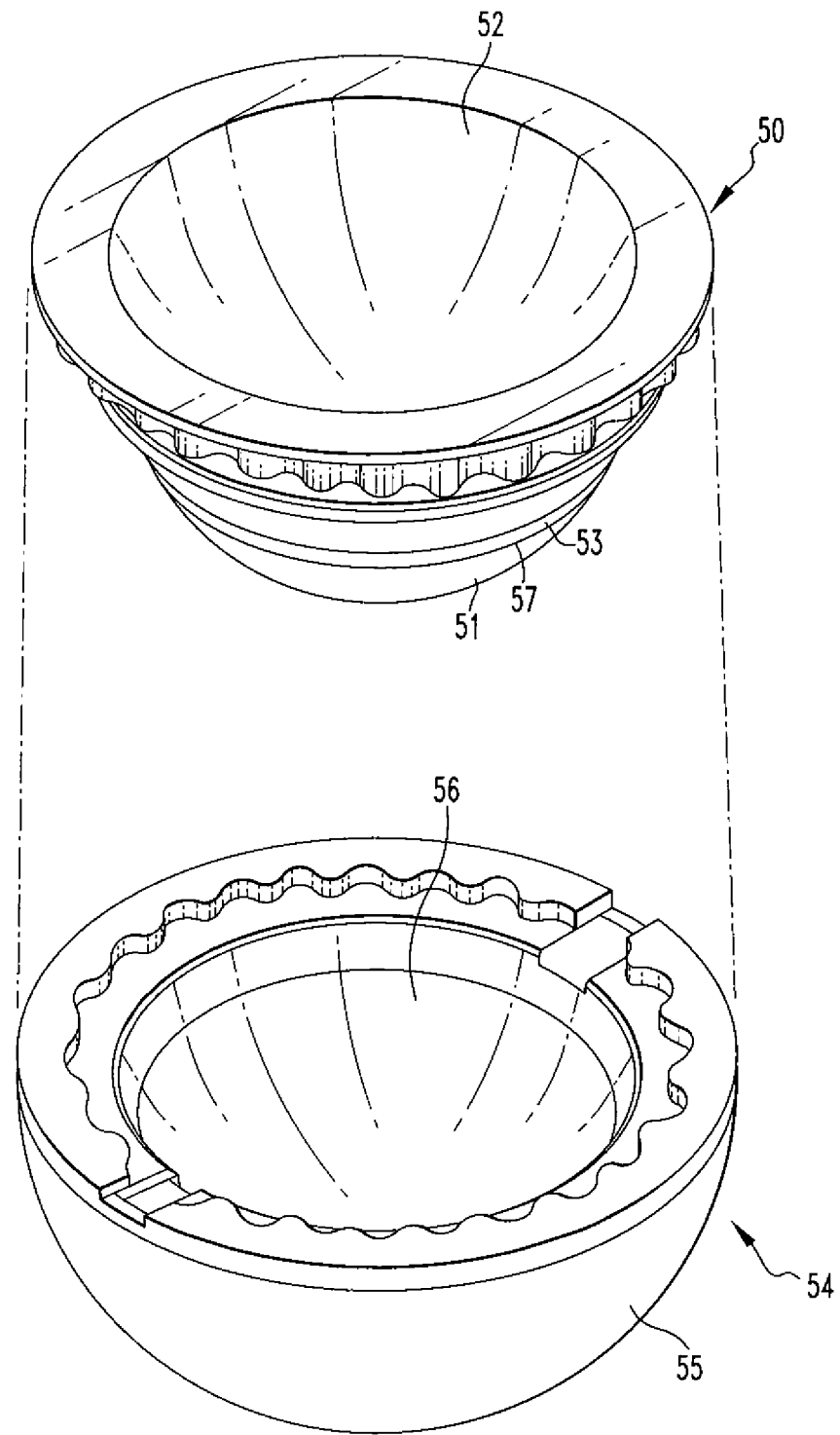
FIG. 6 shows a perspective view of a second embodiment of a liner/prosthetic implant combination of the present disclosure.

Similar to FIG. 5, FIG. 6 shows both an acetabular liner 50 and an acetabular cup 54 having outer surfaces 51,55 and inner surfaces 52,56. The outer surface 51 of the liner 50 includes an indentation 57 that surrounds the entire outer surface 51. Located within the indentation 57 is a shape memory polymer material 53. Once the liner 50 is located within the inner surface 56 of the cup 54, the polymer material 53 may be provided with energy to deform, or expand, the material radially towards the inner surface 56 of the cup 54, thereby fixating the liner 50 to the cup 54. The shape memory polymer material 53 may be resorbable or non-resorbable. The indentation 57 and polymer material 53 may surround less than the entire outer surface 51 of the liner 50 and may be located anywhere on the outer surface 51. In addition, the polymer material 53 may be in a variety of shapes and sizes. Furthermore, it is within the scope of FIG. 6 that the outer surface 51 may not include an indentation, but rather another marking that the polymer material 53 may then be located within. Additionally, the liner 50 may include a smooth outer surface 51 that the polymer material 53 is located on.

Figure 7:
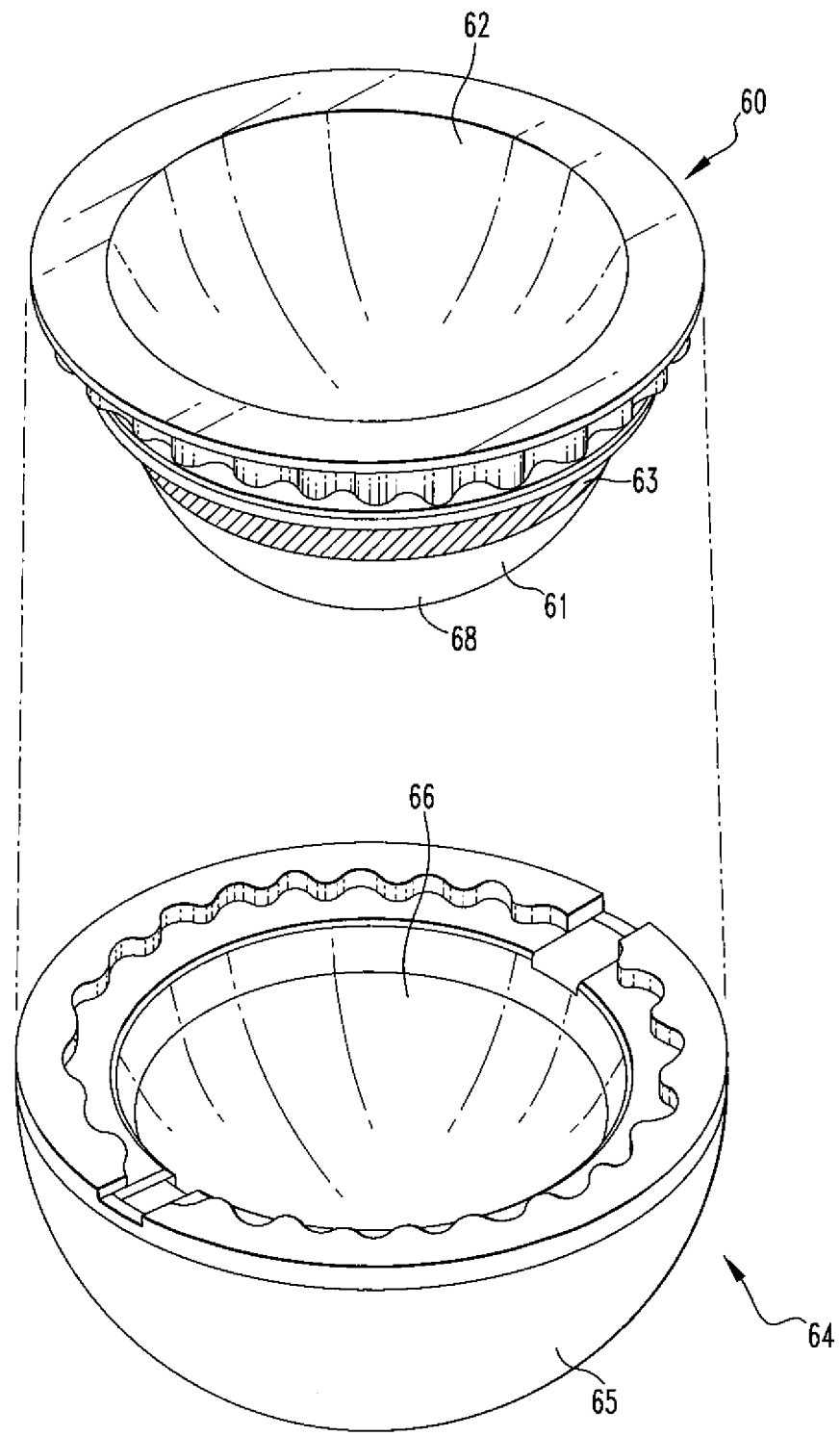
FIG. 7 shows a perspective view of a third embodiment of a liner/prosthetic implant combination of the present disclosure.

Similar to FIGS. 5 and 6, FIG. 7 shows both an acetabular liner 60 and an acetabular cup 64 having outer surfaces 61,65 and inner surfaces 62,66. The outer surface 61 of the liner 60 includes alternating sections of a polymer material having shape memory qualities 63 and a polymer material having non shape memory qualities 68. Once the liner 60 is located within the inner surface 66 of the cup 64, the shape memory polymer material 63 may be provided with energy to deform, or expand, the material 63 radially towards the inner surface 66 of the cup 64, thereby fixating the liner 60 to the cup 64. Both the shape memory polymer material 63 and the non shape memory polymer material 66 may be resorbable or non-resorbable. The outer surface 61 of the liner 60 may include more than two sections of polymer material that may be configured in any number of ways.

Figure 8:
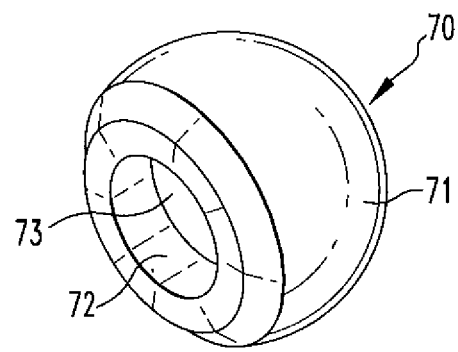
FIG. 8 shows a perspective view of a femoral head of the present disclosure.

In another aspect of the present disclosure, FIG. 8 shows a head 70 for use on an intramedullary implant. The head 70 includes an outer surface 71, an inner surface 72, and an opening 73. Similar to the device 10, or peg, of FIGS. 2A and 2B and the liner 60 of FIG. 7, the head may include alternating sections of a polymer material having shape memory qualities and a polymer material having non shape memory qualities. Alternatively, similar to the liner 50 in FIG. 6, the head 70 may include a non-polymer or a non shape memory polymer material and an indentation filled with shape memory polymer material. The polymer-filled indentation may surround the entire inner surface 72 of the head 70. However, the indentation and polymer material may surround less than the entire inner surface 72 of the head 70 and may be located anywhere on the inner surface 72. In addition, the polymer material may be in a variety of shapes and sizes. Furthermore, it is within the scope of FIG. 8 that the inner surface 72 may not include an indentation, but rather another marking that the polymer material may then be located within. Additionally, the head 70 may include a smooth inner surface 72 that the polymer material is located on.

Figure 9:
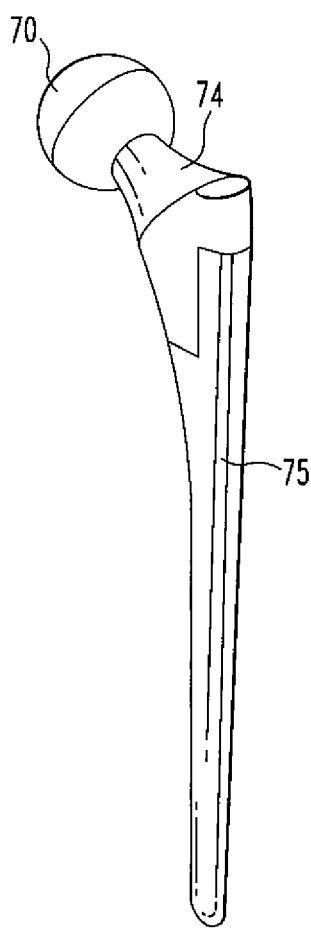
FIG. 9 shows a perspective view of an intramedullary implant having a head of FIG. 8.

As shown in FIG. 9, the head 70 may be placed on the neck 74 of an intramedullary, or femoral, implant 75 such that the neck 74 is inserted into the opening 73 on the head 70. After placement of the head 70 on the neck 74, the shape memory polymer material is provided with energy to deform, or expand, the shape memory polymer material and fixate the head 70 to the neck 74. Alternatively, shape memory polymer material may be placed on the neck 74 of the implant 75, so that after placement of the head 70 on the neck 74, the material may be provided with energy and deformed to fixate the head 70 to the neck 74.

Figure 10:
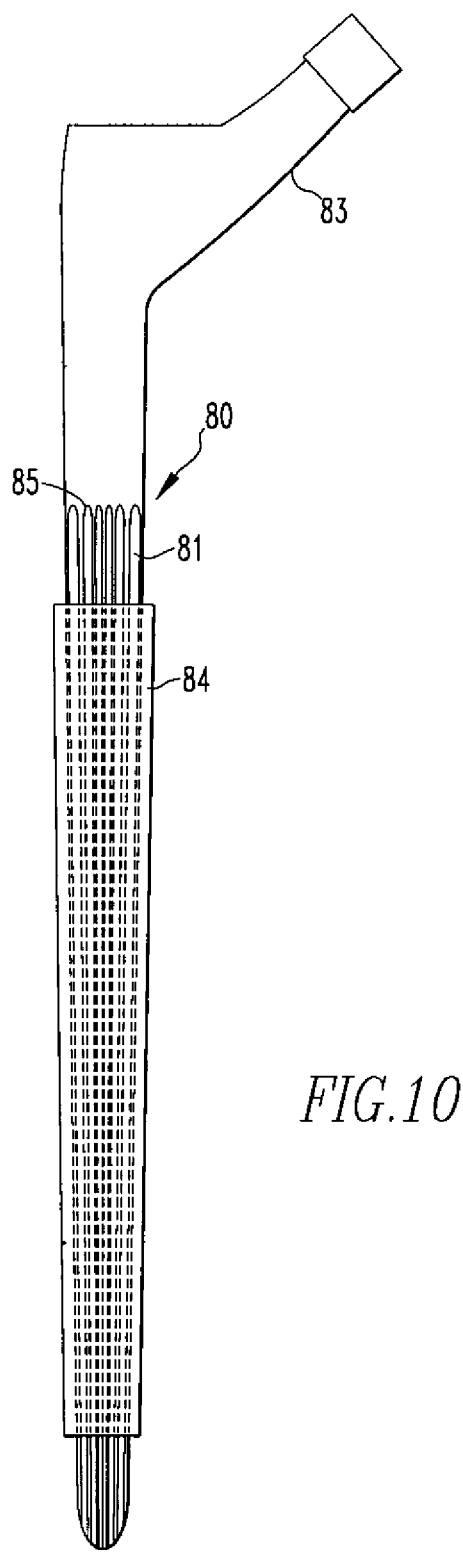
FIG. 10 shows an intramedullary implant of the present disclosure having an interface portion and a polymer material coupled to the interface portion.

In another aspect of the present disclosure, FIG. 10 shows a femoral implant 80 that includes a shaft 81, a polymer material 84 coupled to the shaft 81, and a neck 83. The shaft 81 has a round shape, but could be of any other shape known to one of ordinary skill in the art. These shapes include, but are not limited to, circular, triangular, rectangular, star-shaped, oval, hexagonal, or Chinese star shaped. In addition, a surface of the shaft 81 includes axial grooves 85. However, the surface may include other types of interfaces, such as, but not limited to, radial grooves, helical grooves, screw threads, circumferential ribs, engravings, and otherwise porous or roughened interfaces.

These shapes and surfaces allow formation of bonds between the polymer material and the shaft once the polymer material is provided with energy, as described above. In addition, these shapes and surfaces help the polymer material engage the implant to provide support for axial and torsional loading and to substantially reduce motion in those directions after the implant has been placed in a bone. The shapes and surfaces can be machined, molded, cast, laser cut, or chemically etched into the implant or formed via another method known to one of ordinary skill in the art. Machining of the shapes and surfaces could take many forms, including wire and ram electrical discharge machining (EDM). In addition, the polymer material may be located anywhere along the shaft.

For the purpose of FIG. 10, the polymer material is in the form of a sleeve having a cylindrical structure with an outside surface that is circular and a channel having a circular shape to match the circular shape of the shaft. However, the structure of the sleeve and the channel may have another shape. The sleeve may be formed by die-drawing or molding (i.e. compression flow molding or thermoforming process) the above-mentioned polymers or polymer compositions. The channel may be formed in the sleeve during the die drawing or molding process. Alternatively, the channel may be formed in the sleeve post processing by drilling or by any other method of forming the channel.

In addition, the polymer material may not be in the form of sleeve, but rather there may be several strips of polymer material each of which have a structure and each of which are coupled to the shaft. For example, a shaft having axial grooves, such as the shaft shown in FIG. 10, would have strips of polymer material coupled to the grooved areas. The strips may be formed by the processes listed above or by another process, such as an extrusion process (i.e. single screw, twin screw, disk, ram, or pulltrusion process). However, the polymer material may be in other forms other than the sleeves or strips.

Furthermore, for the purposes of this disclosure, the outer surface of the polymer may be flush, or form the same plane with, the outer surface of the shaft. However, the outer surface of the polymer material may be of a larger diameter than the outer surface of the shaft. The implant may be manufactured from a metal, such as titanium, titanium alloys, steel, stainless steel, cobalt-chromium alloys, tantalum, magnesium, niobium, nickel, nitinol, platinum, silver, zirconium, and combinations thereof. Other metals known to one of ordinary skill in the art could also be used. The implant may also be manufactured from a resorbable or non-resorbable polymer material and may be the same polymer material used on the shaft, as described above, or another type of polymer material.

Figure 11:
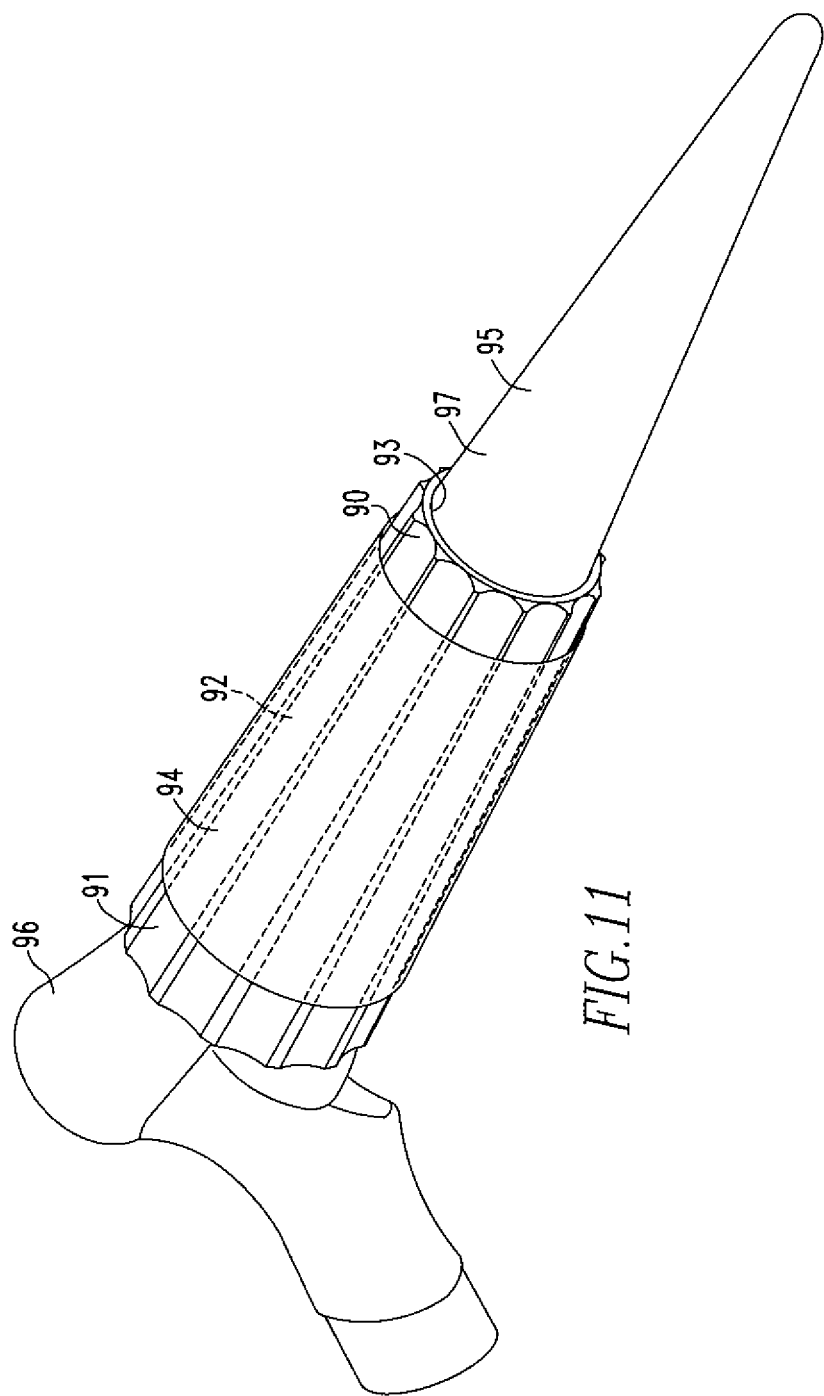
FIG. 11 shows a sleeve of the present disclosure located on the shaft of an intramedullary device.

In another aspect of the present disclosure, FIG. 11 shows a sleeve body 90 for use with an intramedullary implant, such as a femoral implant. The sleeve body 90 includes an outer surface 91, a shape memory polymer material 92 coupled to the outer surface 91, and an inner surface 93. The sleeve body 90 may include the same shapes and the outer surface 91 may include the same surface features of the shaft described above. In addition, as described above, the shape memory polymer material may also be in the form of a sleeve as shown, or in the form of strips that are located on the outer surface 91, possibly between the grooves 94. FIG. 11 also shows an intramedullary implant 95, such as a femoral implant, having a shaft 97 and a neck 96. The sleeve body 90 is located on the shaft 97 such that the inner surface 93 of the sleeve body 90 covers at least a segment of the shaft 97. The sleeve body 90 may be located anywhere along the shaft 97. After placement of the sleeve body 90 on the shaft 97 of the implant 95, insertion of the implant 95 into bone may occur and the shape memory polymer material 92 may then be provided with energy to deform the material 92 and fixate the implant 95 to bone. In an embodiment, a sleeve of shape memory polymer material or strips of shape memory polymer material, as discussed above, may be located on a wall of the inner surface 93 of the sleeve body 90. The material may be provided with energy to deform the material and fixate the sleeve body 90 to the implant 95.

Figure 12:
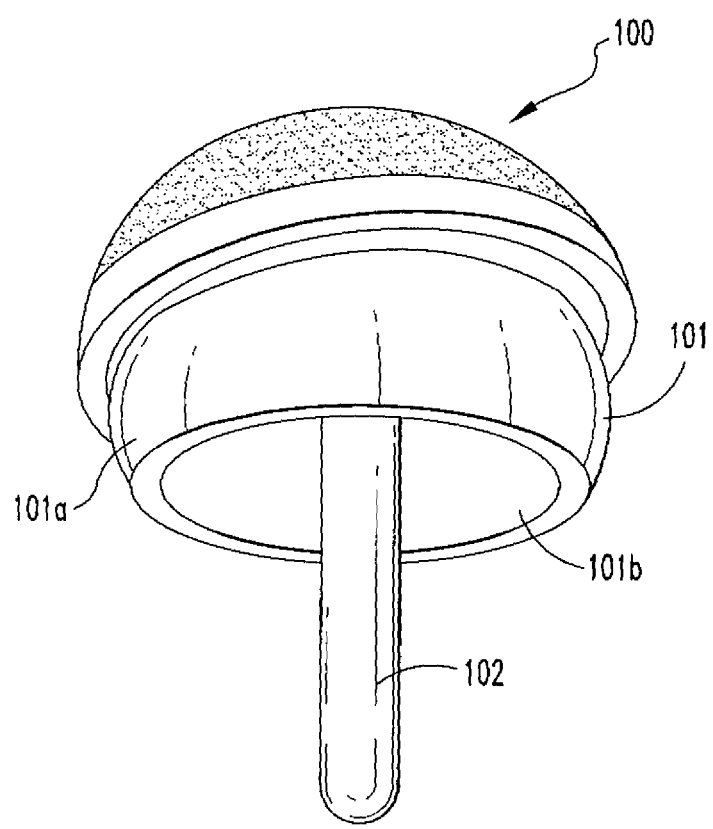
FIG. 12 shows a perspective view of a hip implant.

FIG. 12 shows a hip implant 100. The hip implant 100 includes a shell 101 and a stem 102. The shell 101 includes an outer portion 101a and an inner portion 101b. The stem 102 includes a resorbable shape memory polymer material and is coupled to the inner portion 101b of the shell 101 via a method known to one of ordinary skill in the art. The stem 102 may include alternating sections of a shape memory polymer material and a non-shape memory polymer material, the shape memory polymer material and the non-shape memory polymer material both being resorbable. The implant 100 is utilized in hip resurfacing techniques. In use, the stem 102 is used as a guide for locating the shell 101 on the femoral head. Once the shell 101 is located on the head, the stem 102 is provided with energy, via one of the methods described above or another method known to one of ordinary skill in the art, to deform the stem 102 and create fixation of the stem 102 to the bone. Over time, the stem 102 is resorbed. Resorption of the stem 102 minimizes loading along the stem 102, thereby decreasing stress shielding. Stress shielding occurs when an abnormal loading pattern exists along the articular ridge of a joint. The shell 101 includes a metal material, such as cobalt chrome.

As various modifications could be made to the exemplary embodiments, as described above with reference to the corresponding illustrations, without departing from the scope of the present disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A device for stabilization of a prosthetic implant in bone tissue comprising:
   at least one resorbable component, the resorbable component including a polymer material, the polymer material having shape memory qualities; and
   at least one non-resorbable component; and
   wherein the polymer material comprises a shape memory polymer material having an initial deformed shape and a memorized shape, said shape memory polymer material transforming from said initial deformed shape to said memorized shape upon addition of energy; and
   wherein the resorbable component includes multiple zones of the polymer material having different rates of resorption.

2. The device of claim 1 wherein the shape memory polymer material deforms from the initial deformed shape to the memorized shape upon the addition of heat energy for fixation of the device to the bone tissue.

3. The device of claim 1 wherein the non-resorbable component comprises a metal material.

4. The device of claim 1 wherein the resorbable component includes alternating sections of the shape memory polymer material and a polymer material that does not have shape memory qualities.

5. The device of claim 1 wherein the shape memory polymer material deforms from the initial deformed shape to the memorized shape upon the addition of energy for fixation of the device to the bone tissue.

6. The device of claim 5 wherein deformation of the polymer material comprises outward expansion along a width dimension from the initial deformed shape to the memorized shape.

7. The device of claim 6 wherein deformation of the polymer material comprises axial shrinkage along a length dimension from the initial deformed shape to the memorized shape.

8. The device of claim 5 wherein deformation of the polymer material comprises formation of a bend along a length dimension from the initial deformed shape to the memorized shape.

9. The device of claim 1 wherein the resorbable component includes alternating sections of a first polymer material comprising the shape memory polymer material and a second polymer material that does not have the shape memory qualities.

10. The device of claim 1 wherein the resorbable component includes alternating sections of a first polymer material having the shape memory qualities and a second polymer material that does not have the shape memory qualities, wherein the resorbable component includes sections of the second polymer material arranged on opposite sides of a section of the first polymer material.

11. The device of claim 10 wherein the section of the first polymer material comprises a shape memory polymer material having an initial deformed shape and a memorized shape, the shape memory polymer material transforming from the initial deformed shape to the memorized shape upon addition of energy; and
   wherein the sections of the second polymer material do not change shape upon the addition of energy.

12. The device of claim 11 wherein the initial deformed shape of the section of the first polymer material has a width dimension that is substantially equal to a width dimension of the sections of the second polymer material; and wherein the memorized shape of the section of the first polymer material has a width dimension that is greater than the width dimension of the sections of the second polymer material.

13. The device of claim 11 wherein the shape memory polymer material deforms from the initial deformed shape to the memorized shape upon the addition of heat energy for fixation of the device to the bone tissue.

14. The device of claim 1 wherein the proximal most zone of the polymer material has a slower rate of resorption relative to the distal most zone of the polymer material.

15. The device of claim 1 further comprising an implant; and wherein the device comprises a peg including an attachment portion and a peg portion, the attachment portion comprising the non-resorbable component and attached to the implant, the peg portion comprising the resorbable component and extending outwardly beyond an outer surface of the implant for positioning within the bone tissue.

16. The device of claim 15 wherein the implant comprises an acetabular cup.

17. The device of claim 1 further comprising an implant; and wherein the implant comprises an acetabular cup, and wherein the device comprises a peg extending outwardly from an outer surface of the acetabular cup for positioning within the bone tissue, the peg comprising the at least one resorbable component.

18. The device of claim 17 wherein the acetabular cup includes an opening, the peg extending through the opening for positioning within the bone tissue.

19. The device of claim 17 wherein the non-resorbable component does not extend outwardly beyond the outer surface of the acetabular cup.

20. The device of claim 17 wherein the polymer material of the resorbable component comprises a shape memory polymer material having an initial deformed shape and a memorized shape, the shape memory polymer material transforming from the initial deformed shape to the memorized shape upon addition of energy.

21. The device of claim 17 wherein the acetabular cup includes an opening, the peg including a proximal shoulder comprising the non-resorbable component, the resorbable component extending distally from the proximal shoulder and through the opening in the acetabular cup for positioning within the bone tissue.

22. The device of claim 1 wherein the resorbable component and the non-resorbable component define an interface portion therebetween including a porous surface.

23. The device of claim 1 wherein the polymer material includes a bone growth promoting material for release during deformation or degradation of the resorbable component.

* * * * *